US00PP09877P

United States Patent [19]

Jacobsen

[11] Patent Number: Plant 9,877

[45] Date of Patent: Apr. 29, 1997

[54] POINSETTIA PLANT PETERSTAR MARBLE

[75] Inventor: Peter Jacobsen, deceased, late of Skibby, Denmark, by Aase Jacobsen, executrix

[73] Assignee: Paul Ecke Ranch, Inc., Encinitas, Calif.

[21] Appl. No.: 502,422

[22] Filed: Jul. 10, 1995

[51] Int. Cl.[6] ..... A01H 5/00

[52] U.S. Cl. ..... Plt./86.1

[58] Field of Search ..... Plt./86.1

[56] References Cited

U.S. PATENT DOCUMENTS

P.P. 7,249 6/1990 Neuhaus ..... Plt./86.1

P.P. 9,315 10/1995 Zerr ..... Plt./86.1

P.P. 9,316 10/1995 Zerr ..... Plt./86.1

*Primary Examiner*—James R. Feyrer

*Attorney, Agent, or Firm*—Arnold, White & Durkee

[57] ABSTRACT

Poinsettia 'Peterstar Marble' is a new cultivar, distinguished by bicolored pink and creamy white bracts, large flowers, strong stems and self-branching characteristics. 'Peterstar Marble' is a sport of the red bracted 'Peterstar' (U.S. Pat. No. P.P. 8,259) with the same flowering response and cultural requirements. The new plant produces a very desirable branched flowering pot plant. The new plant is resistant to epinasty after being confined to shipping containers. The post-production foliage and bract retention is good.

1 Drawing Sheet

BACKGROUND OF THE NEW PLANT

This new poinsettia cultivar originated as a bicolored pink on white bracted sport of 'Peterstar' (U.S. Plant Pat. No. 8,259) in my greenhouse in Skibby, Denmark in 1991. It was induced through irradiation of vegetative plants with 2500 rads of gamma radiation, and was selected from about 200 mutants so produced, because of it bicolored pink on white bracts, large flowers, strong stems, self-branching, and dark green leaves, traits which help distinguish it from other poinsettia cultivars, and seemed to make it a desirable plant for commercial greenhouse production. 'Peterstar Marble' differed from its parent 'Peterstar' in having bicolored pink on white bracts as compared to the bright red bracts of 'Peterstar'. 'Peterstar Marble' resembles poinsettia '13-86'. (U.S. Plant Pat. No. 7,249) but differs in color, growth habit and flowering response. The pink color of the flower bracts is brighter and the relative area of pink color on each bract is larger for 'Peterstar Marble' than for '13-86 '.

The foliage and bract colors and the flowering response of 'Peterstar Marble' are distinctly different from known poinsettias of similar derivation. The leaf color of 'Peterstar Marble' is darker than 'Fispue' (U.S. Plant Pat. No. 9,315) and more yellow green in color than 'Fispla' (U.S. Plant Pat. No. 9,316). The pink bract color of 'Peterstar Marble' is brighter and the flower response time is shorter than either 'Fispue' or 'Fispla'.

After selection, 'Peterstar Marble' was vegetatively reproduced from stem cuttings for test purposes in Encinitas, Calif. By subjecting clones of this plant to successive generations of vegetative propagations, it was demonstrated that the distinctive characteristics of 'Peterstar Marble' held true from generation to generation. Grown under the same greenhouse environment, 'Peterstar Marble' had the same growth habit and flowering response time as the parent plant 'Peterstar'.

DESCRIPTION OF THE PHOTOGRAPHS

Poinsettia 'Peterstar Marble' is illustrated in the accompaning color photographs.

The upper photo is a side view of 3 single stem plants per pot in full flower.

The lower photo is a top view of the same plants showing flower and bract formation.

DESCRIPTION OF THE PLANT

The following is a detailed description of this new poinsettia as observed in Encinitas, Calif., U.S.A. during December 1994. Observations were recorded from flowering plants, grown as 3 single stem plants per pot. The pot was 14 cm in diameter and 11 cm in height. Color designations are compared to the 1986 edition of R.H.S. Colour Chart, first published in 1966 by The Royal Horticultural Society, London, England.

THE PLANT

The following chart summarizes some of the differences between 'Peterstar Marble' and poinsettia '13-86'.

| Plant | 'Peterstar Marble' | '13–86' |
|---|---|---|
| Internode Length | 16–17 mm | 20 mm |
| Height | 35 cm | 40 cm |
| Flower Response | 8.5 weeks | 9 weeks |
| Blooming date (Southern California) | November 25 | November 30 |
| Flowers | Sterile | Fertile |
| Bract Color | RHS 8D and RHS 52B | RHS 155A and RHS 51C |

Chart II below further illustrate differences between 'Peter Marble' and other related cultivars. Comparisons of leaf and bract colors and flower responses for 'Peterstar Marble' in comparison to 'Fispue' and 'Fispla' are as follows:

CHART II

| | 'Peterstar Marble' | 'Fispue' | 'Fispia' |
|---|---|---|---|
| Leaf | | | |
| upper: | darker 147A | 137A–147A | 139A |
| under: | 147B | 137C | 137C |
| Bract | | | |
| upper-pink: | 52B | 51C | 51B and 51C |
| upper-white: | 8D | | |
| Flowering Response: | 8.5 weeks | 9 weeks | 9–10 weeks |
| Leaf Petiole Length: | 4–6 cm | 8 cm | 8.5 cm |

Additionally, the percent of bract surface that is pink is greater for 'Peterstar Marble' than 'Fispue' and much greater than 'Fispla'. Plant height of the flowering plants is comparable for 'Peterstar Marble' and 'Fispue' are taller than 'Fispla'.

Phenotypically, 'Peterstar Marble' resembles its parent 'Peterstar' (U.S. Plant Pat. No. 8,259) in virtually all respects except those traits associated with color mutations. The morphology, plant vigor and flowering response times are very similar. The flower bract color of 'Peterstar Marble' is bright pink and white. The red bract color of 'Peterstar' is near R.H.S. 46B. The leaf petiole color of 'Peterstar Marble' is light green, that of 'Peterstar' is red.

Origin: Sport of 'Peterstar' (U.S. Plant Pat. No. 8,259), induced through irradiation of vegetative plants with 2500 rads of gamma radiation.

Classification:

*Botanic.*—*Euphorbia pulcherrima* Willd.

*Common name.*—Poinsettia.

*Cultivar name.*—'Peterstar Marble'.

Form: Shrub.

Height: Medium.

Growth habit: As a single stemmed plant, upright and vigorous with self-branching side shoots. The application of a chemical growth retardant may not be needed to restrict height for commercial pot plant production. I observed 3 unpinched plants in a pot with an overall height of 35 cm and an overall width of 45 cm. The bract diameter of individual flowers was 30 cm. The compactness of 'Peterstar Marble' is demonstrated by the internode length. The internode length of 'Peterstar Marble' was 16–17 mm.

Branching: Axillary branches will develop and terminate in a flower without pinching. However, it is usually desirable to pinch 'Peterstar Marble' before flower induction and remove all terminal dominance. Then, all axillary branches will develop uniformly and at a faster rate.

Growth rate: Rooting of stem cutting occurs in 12–18 days under intermitten mist.

Flowering: The plant will flower in eight to nine weeks under continuous long night conditions and night temperatures of about 16°–18° C. Like its parent, ('Peterstar'), 'Peterstar Marble' will be in full bloom in late November in the Southern California under natural daylength conditions.

Foliage: The foliage was clean and uniformly dark green from bottom to top of the plant. The leaves were of medium size, leaf blades tpically being 13–14 cm long and 8–9 cm wide with leaf petioles 4–6 cm long.

*Leaf shape.*—Typical leaves are ovate with obtuse bases and acuminate tips. Leaf margins are mostly entire. An occasional lower leaf is modestly lobed on either side of the leaf blade.

*Leaf surface.*—The upper surface is glabrous and the under surface is slight pubescent.

*Color.*—Upper side — Green, slightly darker than R.H.S. 147A. Under side — Green, near R.H.S. 147B.

*Retention.*—The foliage retention is good even under low light intensities in the consumer's home.

Bracts: Generally there were 17–21 bicolored pink on white bracts of various sizes subtending the cyathia. The primary bracts had blades tpically 14–16 cm long and 10–11 cm wide with petioles 2–3 cm long.

*Shape.*—Primary bracts are ovate with acute bases and acuminate tips. Leaf margins are entire or weakly lobed with 1 small indention on either side of the bract. Secondary bracts are ovate to elliptic and have entire margins.

*Surface.*—The bract surface is slightly rugose.

*Color.*—Upper side — Bicolored: Pink and creamy white on each bract. An irregular area of pink, near R.H.S. 52B, is located at the center of the bracts, usually on either side of the mid-vein. The creamy white color, near R.H.S. 8D, is preipheral to the pink. Under side — Bicolored: Pink and creamy white. The patterns of each color mostly mirror the upper surface. The pink is near R.H.S. 52B and the peripheral white is near R.H.S. 8D.

Flowers: Generally, 18–22 cyathia (flowers) are present when the plant is in full bloom. Each cyathium is about 6–7 mm long and 5–6 mm wide, green in color, and fringed yellow at the distal end. Usually one, but occasionally two, yellow nectar cups protrude from the side of each cyathium. The flower pedicel is also green and about 5 mm in length. The stamens protruding from the cyathia are pink. The stigmas are greenish white and trifurcate. 'Peterstar Marble' has abortive anthers, is male sterile and possible female sterile, as seed set has not been seen on this cultivar. Cyathia retention is about three weeks beyond the time the flower is fully mature.

*Nectar exudate.*—Present, abundant.

*Seed formation.*—No seed set observed.

*Fertility.*—Flowers may be sterile.

Post production: 'Peterstar Marble' is resistant to epinasty after being confined to shipping containers. The foliage and bract retention is good.

What is claimed is:

1. A new and distinct poinsettia cultivar, substantially as herein shown and described, distinguished by its strong stems, bicolored pink and creamy white bracts, self-branching, large flowers and good leaf and bract retention in the consumer environment.

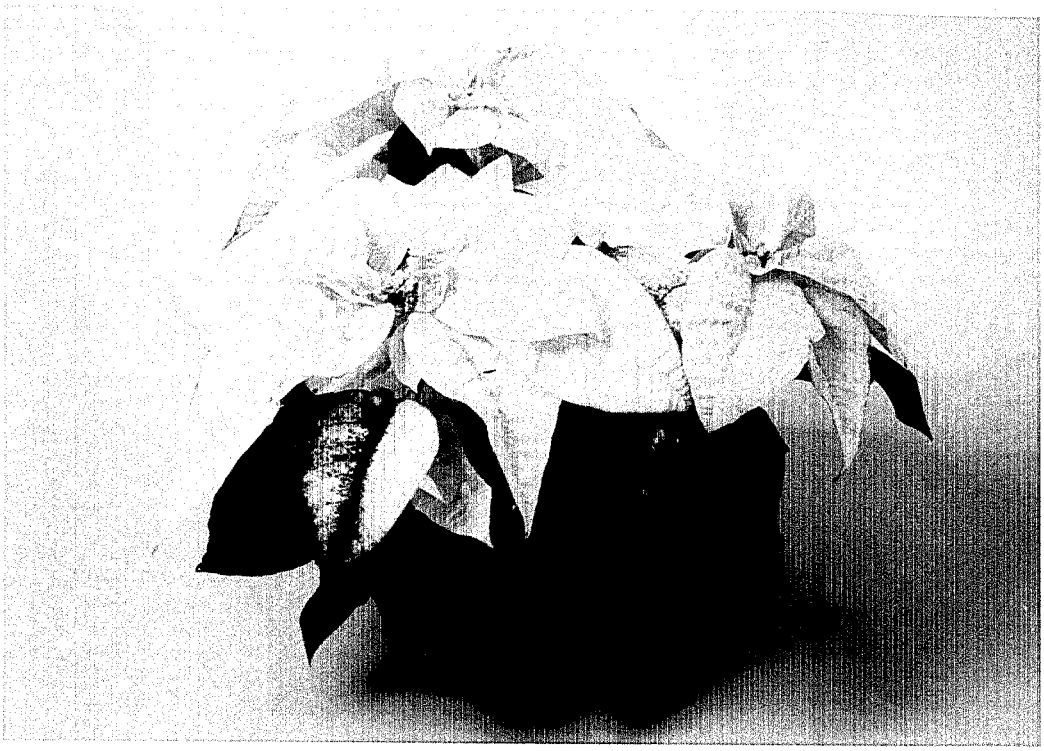
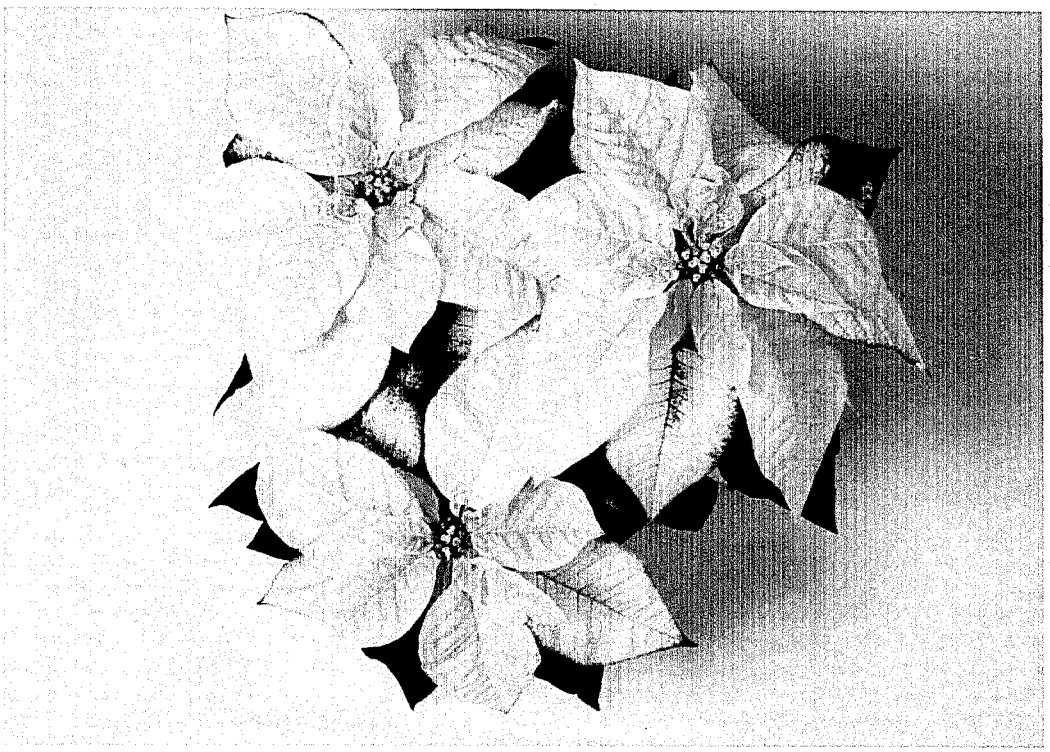

* * * * *